United States Patent
Hoffmann et al.

[11] Patent Number: 5,914,295
[45] Date of Patent: Jun. 22, 1999

[54] IMPLANTABLE MOLDED ARTICLES FOR THE ADMINISTRATION OF ACTIVE SUBSTANCES TO PLANTS

[75] Inventors: Hans-Rainer Hoffmann, Neuwied; Malgorzata Kloczko, Linz; Michael Roreger, Neuwied, all of Germany

[73] Assignee: LTS Lohmann Therapie-Systeme GmbH, Neuwied, Germany

[21] Appl. No.: 08/809,656

[22] PCT Filed: Sep. 4, 1995

[86] PCT No.: PCT/EP95/03473

§ 371 Date: Jun. 11, 1997

§ 102(e) Date: Jun. 11, 1997

[87] PCT Pub. No.: WO96/07311

PCT Pub. Date: Mar. 14, 1996

[30] Foreign Application Priority Data

Sep. 9, 1994 [DE] Germany .............. 44 32 126

[51] Int. Cl.[6] .......... A01N 25/34; A01N 25/10; A01G 7/06
[52] U.S. Cl. .............. 504/116; 47/47.5; 47/58; 424/411; 514/953
[58] Field of Search .............. 504/116; 47/47.5, 47/58; 424/411; 514/953

[56] References Cited

U.S. PATENT DOCUMENTS

| | | | |
|---|---|---|---|
| 3,074,207 | 1/1963 | Laing | 47/57.5 |
| 3,647,416 | 3/1972 | Messman | 71/29 |
| 4,014,541 | 3/1977 | Desmarais | 273/33 |
| 4,078,087 | 3/1978 | Hyman | 424/329 |
| 4,126,438 | 11/1978 | Pulli et al. | 71/3 |
| 4,338,746 | 7/1982 | Sarett | 47/58 |
| 4,590,062 | 5/1986 | Jang | 424/19 |
| 4,766,695 | 8/1988 | Harlow | 47/24 |
| 5,317,037 | 5/1994 | Golden et al. | 523/128 |
| 5,660,851 | 8/1997 | Domb | 424/427 |

FOREIGN PATENT DOCUMENTS

| | | |
|---|---|---|
| 31497/84 | 8/1984 | Australia . |
| 1 089 645 | 11/1980 | Canada . |
| 48-1178 | 1/1973 | Japan . |

*Primary Examiner*—S. Mark Clardy
*Attorney, Agent, or Firm*—Wenderoth, Lind & Ponack, L.L.P.

[57] ABSTRACT

Implantable, partially biodegradable, polymer-containing molded articles for the administration of active substances to plants are characterized by the fact that they comprise at least one hydrophobic polymer.

20 Claims, 2 Drawing Sheets

▓▓ ACTIVE SUBSTANCE A
▓▓ ACTIVE SUBSTANCE B

IMPLANTABLE MOLDED ARTICLES FOR THE ADMINISTRATION OF ACTIVE SUBSTANCES TO PLANTS

This application has been filed under 35 USC 371 as the national stage of international application PCT/EP95/03473, filed Sep. 4, 1995.

BACKGROUND OF THE INVENTION

The present invention relates to implantable, partially biodegradable polymer-containing molded articles for the administration of active substances to plants.

In contrast with human and veterinary medicine it is rather unknown to administer active substances to plants by means of implantable devices. The active substance formulations used in general practice are either sprayed on the plant or brought into the soil near the roots. These conventional application forms have the disadvantage that great amounts of the active substance is last during application; this result in a considerable environmental impact (contamination of the air, soil and waters) require larger amounts of active substances.

This disadvantageous active substance loss is of particular weight when plant protection measures are to be taken on urban regions (trees in avenues, municipal park grounds), or when they have to be repeated for several times during one vegetation period, for example, in agricultural plants with high degree of pest infestation.

In order to minimize the risks of environmental pollution during plant treatment and to achieve a prolonged duration of action of the active substances, various alternative active substance release systems have been developed. For example, those described in the patent specifications of EP 0 254 196 and DE 39 22 366. These relate to devices for the transcuticular or transperidermal application of systemic active substances to plants. These are sustained-release depot preparations in the form of flat-shaped, patch-like, adherent and pressure-sensitive adhesive systems which are suitably applied on a chosen site of the plant shoot axis. In addition, there are the active substance administration forms according to DE-GM 17 60 060 and U.S. Pat. No. 4,766,695. These are simple tree rings comprising insect repellents or insecticides giving external protection to the plant. The above-mentioned publications do not clearly indicate that these are systems for a systemic administration of active substances; however, because of their construction and composition, it is obvious that they can have this function.

The above-mentioned active substance release systems are applied externally onto the plant surface. For this reason, they have the disadvantage that their functional capability which is based on perfect adhesion is influenced by environmental factors. In addition, these devices have to be removed after depletion of the systems. Moreover, this type of application does not present a satisfactory take-up of active substances since absorption is impeded by barriers in the form of terminal tissue which is difficult to permeate.

The direct administration of active substances into the conductive system of the plant by means of an injection—as described in the patent documents U.S. Pat. No. 4,078,087; U.S. Pat. No. 4,103,456; CA 1,089,645, and U.S. Pat. No. 3,576,276—can overcome the above drawbacks; however it involves other deficiencies. Since the active substance release is effected very rapidly and directly into the conductive system, there is the potential risk of excessive active substance concentrations involving plant damages. Another disadvantage is the fact that several repeated treatments are necessary to ensure the required active substance concentration at the site of action over a longer period. These drawbacks can be avoided by using release devices positioned in the interior of the plant and ensuring continuous and long-term supply of active substances at the same time.

Administering active substances to plants by means of implantable application systems has been mentioned in the relevant literature (patent document AU 8431497 and JP 58039602); however, they have not attained commercial status so far.

The publication AU 8431497 relates to an implantable device in the form of a porous ceramic body positioned in a mechanically provided hole in the trunk and connected with an external active substance reservoir by means of capillaries. The active substance release which is effected in two steps, i.e. transport from the reservoir and passage through the porous body, is carried out by utilizing the pressure in the conductive vessels generated by transpiration and the capillary forces of the porous implant. For this reason, the main disadvantage of such an application system is the fact that the active substance release to the plant exclusively depends on the water balance of the plant, and this may result in an excessive active substance concentration if transpiration is intense. If this device is used, the active substance can scarcely be dosed with sufficient accuracy. Moreover, the application of this system is very difficult since the implant body has to be removed after termination of the treatment.

The implantable release system described in JP 58039602 can overcome these disadvantages. It relates to implantable active substance-containing molded articles of different forms (tablets, rods, discs, etc.) consisting of a mixture of highly water-absorbing polymers, such as starch-acrylamide-copolymers, starch-acrylonitrile-copolymers, and hydrophilic polymers, such as ethylene-vinyl acetate-copolymer. These systems are used to release biologically active substances to trees; amongst other things, to combat diseases requiring long-term treatments, for example in case of ceratocystis spp. (in *Pinus silvestris*). They are inserted into the cavity (hole) previously bored into the trunk, and remain there for a longer period of time. Swelling caused by excessive water absorption results in a considerable increase in volume, and this results in the fact that the total space available for the implant is filled and the previously formed aperture sealed up. Although the publication gives no direct indication as to a biodegradability of these implants, their chemical composition suggests that they can at least partially be degraded in the plant's organism. For this reason they must be regarded as partially biodegradable within the meaning of this publication, and they have the advantage that they possibly need not be removed from the plants.

However, these systems involve a lot of problems mainly resulting from their chemical constitution. Owing to the fact that they exclusively consist of hydrophilic polymers, they are only partially suitable for incorporating highly lipophilic substances. In particular if a relatively high active substance loading capacity is required, these implant systems are rather unsuitable.

An additional disadvantage is the fact that a hydrophilic polymer matrix, after incorporation into plant tissues with a rather high cell hydration state, releases the active substance relatively fast. This indeed creates high active substance concentrations, but the system is exhausted after a short time. In the practice of administering active substances to plants, for example, in the treatment of periodically appearing diseases with a high risk of infection or pest attack, there are many cases where an effective concentration is to be maintained over a longer period of time. For these applications (for example, scurf attack in apple trees in areas with heavy rainfall, or pest attacks destroying the sprouts in banana plants) polymers are required as carriers, which impart depot properties to the system.

Also, the problem of active substance losses could not be solved in a satisfactory manner in these systems. As mentioned above, producing an intimate contact between the implant body and the boundary surfaces of the plant cavity greatly depends on the water absorption and therefore on the hydration state of the tissue cells at the site of application. As is generally known, the osmotic conditions of plant cells are subject to severe variations according to the demands on the water balance. Extremely low or extremely high water potentials can cause great volume changes of the implant and therefore change the seal tightness of the aperture in the trunk.

Finally, the relatively poor thermoplastic processibility and insufficient mechanical properties are to be mentioned as further drawbacks of these systems; these also result from the hydrophilic character of the skeletal polymers.

SUMMARY OF THE INVENTION

It was the object of the present invention to propose a solution of the above-mentioned problems by providing biodegradable active substance release systems for the intracorporeal application in plants; these are suitable for both a rapid and short-term, and a long-term and persistent active substance release and have satisfactory mechanical properties, and the molding materials serving their production have a perfect thermoplastic processibility.

According to the present invention this object is achieved by molded articles which are implantable, partially biodegradable molded articles which substantially consist of polymers and at least comprise one hydrophobic polymer.

BRIEF DESCRIPTION OF THE DRAWINGS

To illustrate the present invention

FIG. 1 shows a molded article consisting of several compartments (segments) 1, wherein one compartment is surrounded by the next one.

FIGS. 2 and 3 show molded articles wherein the individual segments have an alternating arrangement. In the embodiment of FIG. 2 individual compartments comprise different active substances separated from one another. In the embodiment according to FIG. 3 one compartment comprises two or more different active substances.

FIG. 4 shows a molded article in the form of a nail with an optionally heat-treatable or temperable tip 2 and further compartments 3.

FIG. 5 shows a special embodiment wherein several nail-shaped members 5 are combined to form one application unit by fastening them on a rigid plate 4.

DETAILED DESCRIPTION OF THE INVENTION

Figure 1:
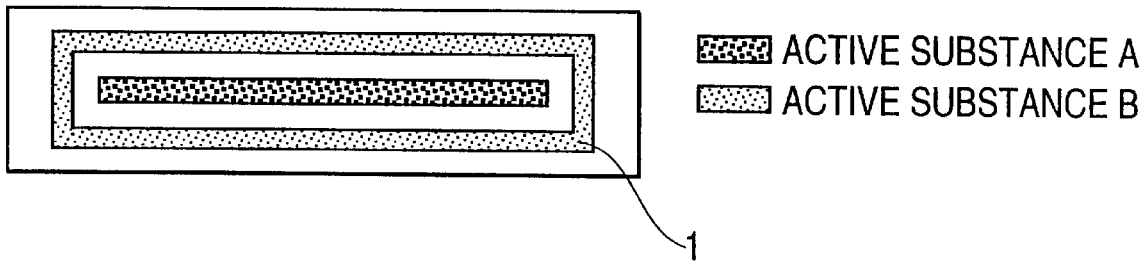
FIGS. 1 to 5 are described in the following.

The term "biologically degradable" used in the present document is equivalent with "biodegradable" and is to be understood as "degradable under stimulation by a biologically active environment".

Therefore, the molded articles are both subject to the metabolism of higher plants and degradable by microbes.

The biological degradation results in simultaneous active substance release and is initiated by bioerosion in the plant. The degradation of the products according to the present invention mainly results in the fragments whose biocompatibility is known; they can be metabolized in natural metabolic pathways of the plant. The intensity and extent of degradation of these bodies in the plant organism depend on the kind of implant materials. For this reason the decomposition period can be adapted to the respective indication requirements by adequate choice of the starting materials. This property, in particular, meets the great variety of horticultural demands with respect to active substance supply since these systems can easily be used both in long-term applications and short-term treatments. Because of their biodegradative ability in higher plants, these products are partially or completely decomposed in the plant within a reasonable period, thus rendering their removal superfluous. In addition, even after withering of the plant they are incorporated into the natural cycle. In comparison with the conventional release systems, this is of particular advantage since they have no adverse effect on the environment. The bodies according to the present invention can partially or completely be degraded in a microbially active environment (i.e. into water, carbon dioxide, and naturally occurring metabolic products).

The biological degradability in the first place concerns polymers which are used as carrier materials in the implants according to the present invention. In this connection, bioactive compounds are embedded in an inert polymer matrix without being chemically combined. The polymers used have a high absorption capacity (loading capacity) for active substances and the required application technological functionality (sufficient mechanical stability and processibility) on the other hand, and which are not phytotoxic and can be mixed with other substances in wide ranges. In this connection, it is absolutely essential that the polymer matrix comprise a hydrophobic polymer.

The following families are particularly suitable as hydrophobic, biologically degradable polymers:

aliphatic polyesters, such as caprolactone, poly(3-hydroxybutanoic acid), polyhydroxybutanoic acid/hydroxyvaleric acid-copolymers, and polylactic acid cellulose derivatives with a degree of substitution of $\leq 2$, such as cellulose ethers, cellulose esters, or cellulose mixed esters polyanhydrides lignin from the Kraft-process chitin An example of an aliphatic polyester is a poly(3-hydroxybutanoic acid)/3-hydroxyvaleric acid-copolymer having a molar mass of 450,000.

Cellulose diethyl ether is an example of a cellulose ether. Cellulose diacetate is an example of a cellulose ester, cellulose acetate butyrate is an example of a mixed ester.

Poly-(1,3-bis-p-carboxy-phenoxy-propane/sebacic acid)-copolymer is an example of polyanhydrides.

All of the proposed hydrophobic polymers have a very high degree of biodegradability and a perfect thermoplastic processibility.

The important advantage of the molded articles according to the present invention—as compared to all known implantable active substance systems described in the art—lies in the fact that the incorporation of hydrophobic polymers into their active substance carrier matrices gives an easy incorporation of highly lipophilic active substances and the possibility of a delayed active substance release.

As is generally known, hydrophilic properties are of great importance in active substance-containing implants because they ensure both rapid bioerosion based on swelling and/or hydrolysis and the resulting rapid active substance release. On the other hand, hydrophilicity of such systems is rather undesired with respect to incorporating highly lipophilic bioactive substances. Using hydrophobic polymers, serving as mediator phase in the dispersion of active substances, achieves a relatively homogeneous distribution of the incorporated substances.

After having been implanted, the molded bodies, according to the present invention, release active substances in the plant organism. In this connection, the active substances may be released by their diffusion and/or by swelling or bioerosion of the implanted bodies. Since swellability and bioerodibility are positively influenced (activated) by the hydrophilic properties of the polymers, the incorporation of a hydrophobic phase into the polymer composition results in an implant body manufactured thereof having a prolonged residence time in the plant, and therefore a delayed active substance release is achieved. For this reason, the molded articles according to the present invention (depending on the hydrophobic polymer portion) can be used for a slow and sustained active substance release.

Another advantage of the molded articles according to the present invention is the fact that the molding materials used for their production exhibit easy thermoplastic processibility. This improvement in processibility primarily concerns the flowability and viscoelastic behavior of the mass.

In particular, if a polymer composition is present which consists of two immiscible phases and requires the addition of plasticizing agents for good phase intermixing, the improved processibility of the mass caused by the incorporation of the hydrophobic polymers becomes very apparent.

A preferred embodiment of the molded articles according to the present invention has the following components: relative to the total weight of the molded article 0.5 to 90%-wt. of at least one polymer, with the proportion of a hydrophobic polymer amounting to at least 30 to 80%-wt., preferably 50 to 65%-wt., of the polymer content. The ratio between matrix material (polymers) and auxiliary agents, which together form an active substance carrier system of the molded article according to the present invention, can be varied within wide ranges.

A great number of polymers may be used as biodegradable carrier materials. Suitable are polymers of glycolic acid and lactic acid as well as their copolymers (in different weight ratios of the monomer units). Particularly suitable are derivatives of the above-mentioned carboxylic acids of the type polylactides, polyglycolides and their copolymers. Generally suitable are all homo- and copolymers of α-hydroxyfatty acids with 2 to 16 C-atoms and their derivatives, provided that they are absorbable in the plant organism, for example, α-hydroxybutanoic acid, α-hydroxyisovaleric acid, α-hydroxyisocaproic acid, α-hydroxyheptanoic acid, α-hydroxyoctanoic acid, α-hydroxydecanoic acid, and α-hydroxymyristic acid. Particularly suitable among the derivatives of α-hydroxyfatty acids are polyhydroxy valerate and polyhydroxy butyrate as well as their copolymers.

Further suitable polymers for the use as active substance matrix in the molded articles, according to the present invention, are polyamides, with particular preference for polylysine ethyl/methyl ester fumaramide, polylysine methyl ester fumaramide, polylysine ethyl ester fumaramide, and polylysine butyl ester fumaramide.

According to the present invention the biodegradable implants may also comprise naturally occurring polymers as active substance carriers. Particularly suitable are starch, lignin from the Kraft process, chitin, cellulose and its derivatives.

Different biologically degradable polymers may be used as hydrophobic component of the polymer matrix of the molded articles according to the present invention. Examples thereof include:
- aliphatic polyesters, e.g. caprolactone
- cellulose derivatives with a substitution degree of $\leq 2$, e.g. cellulose diethyl ether
- polyanhydrides, e.g. poly-(1,3-(p-carboxy-phenoxy-propane/sebacic acid)-copolymer The active substances which can be released to plants by means of the implantable molded articles according to the present invention include those capable of influencing processes in the animal or plant organism. These mainly include systemically active plant protection agents (insecticides, acaricides, fungicides, and bactericides).

Systemic insecticides include, for example, butocaroxim, di-methoate, fenoxycarb, methamyl, oxamyl, oxydemeton-methyl, pirimicarb, or propoxur.

Systemic acaricides include, for example, clofentizine, fenbutatin oxide, and hexythiazox.

Systemic fungicides include, for example, benomyl, bromuconazole, bitertanole, etaconazole, flusilazol, furalaxyl, fosetyl-Al, imazalil, metalaxyl, penconazole, propiconazole, thiabendazol, triadimefon, triadimenol, or triforine.

Flumequine, for example, is to be mentioned among the systemic bactericides.

Systemic growth regulators include, for example, ethephon and β-indolylacetic acid (IAA).

As is generally known, the above-mentioned systemic active substances can be absorbed by the plant organs (leaves and roots, shoot axis) after application of conventional preparations; and after absorption they can be transported and systemically distributed in the conductive system of the plant.

Further bioactive substances which can be administered by means of the molded bodies according to the present invention are plant restoratives, such as plant extracts from nettle, tansy, horsetail, or herbaceous knotweed; these may have both a local and a systemic action.

The active substances may be present in the molded articles according to the present invention either alone or in admixture with one another. They may be dissolved or dispersed in the inert polymer matrix. Within the scope of the present development there are also many possibilities of varying the particle size of the incorporated active substances. The preferred particle size is the range of <10 μm.

The function of the auxiliary agents is to offer the active substance to the plant in a suitable physical-chemical form so that it is available for the desired therapeutic purpose. Moreover, they produce the optimum effect of the potency inherent in an active substance. The molded articles according to the present invention may comprise as auxiliary agents: penetration enhancers, degradation accelerators, pore-forming agents, pH-regulators, emulsifiers, fillers, plasticizing agents.

Penetration enhancers intensify the absorption of the bioactive substance in the conducting system of the plant. For this purpose the following substances may be added, for example, alkylsulfates, alkyl sulfonates, fatty acids, fatty acid salts of multivalent metals, fatty acid esters, amine oxides, mono-, di- or triglycerides, long-chain alcohols, salicylic acid, 2-pyrrolidone derivatives, or urea.

Degradation accelerators are substances promoting the degradation rate of the implant. Examples of suitable substances which may be added as degradation accelerators to the molded articles according to the present invention include acetates, such as methyl-, ethyl-, n-propyl-, isopropyl-, n-butyl-, isobutyl-, n-pentyl-, and isopentyl ester. Particularly preferred is ethyl acetate, also called acetic ester.

In addition to compounds influencing the degradation rate of the carrier material, the implants according to the present invention also comprise substances in the form of pore-forming agents permitting a control of the active substance release. The active substance can directly diffuse out of the pore system formed in the molded body by means of pore-forming agents, or the process of bioerosion is initiated or accelerated. Suitable pore formers include, for example, water-soluble monosaccharides and disaccharides, such as glucose, fructose, xylose, galactose, sucrose, maltose, saccharose, and allied compounds, such as mannitol and sorbitol. Lactose is particularly preferred.

Suitable pH-regulators according to the present invention are glycin, citrate, borate, phosphate- or citric acid phosphate buffers.

Emulsifiers which can be used include, for example, higher fatty alcohols, partial fatty acid esters, polyvalent alcohols, partial fatty acid esters of sugars, polyethyleneglycol fatty acid esters, polyethyleneglycol sorbitan-fatty acid esters, as well as phospholipides, quaternary ammonium compounds, and pyridinium compounds.

Suitable fillers include aluminum oxide, zinc oxide, titanium oxide, and silicon dioxide.

Processing the molding materials, in particular during phase intermixing and shaping, is facilitated by means of plasticizing agents. Suitable plasticizing agents are, e.g., poly(ethylene glycol)-phenyl ether (Pycal 94), glycerol, sorbitol, palmitic acid, lauric acid, and oleic acid derivatives.

The quantitative and qualitative combination of the polymers and formulation aids, which jointly form a carrier system for the active substance, is decisive for the active substance release; the skilled artisan can make good use of this fact when the desired release rate is set. The preferred alternatives of the molded articles according to the present invention are based on gradually absorbable substances. According to a particular embodiment of the present invention, the carrier matrix of the molded articles is a combination of biodegradable polymers having different molecular weights. By degradation of the polymers having a lower molecular weight, an earlier active substance release takes place, whereas the delayed degradation of polymers having a high molecular weight results in the release taking place at a later time. As low-molecular polymers, the implants according to the present invention may for example be poly-(L(+)-lactic acid), poly-(D-lactic acid), poly-(DL-lactic acid), polyglycolic acid and copolymers of the above-mentioned compounds. The molecular weights of these compounds amount to 1,000 to 4,000, preferably 1,500 to 2,500.

Implants having an additional coating of a low-molecular polymer not comprising an active substance represent another preferred embodiment of the molded articles according to the present invention. This prevents the active substance release from taking place too fast in the initial phase after implantation.

It is also possible to control the degradation rate of the implant and thereby the active substance release in the desired manner by incorporating suitable biologically inactive groups, e.g., organo-metallic compounds, into the active substance carrier system.

Particularly advantageous are molded articles according to the present invention which are based on polyester. With these it is possible to control their degradation rate indirectly by the number of ester bonds. As is generally known, the carboxyl groups resulting after enzymatic or hydrotic ester cleavages increase the hydrophilicity of the matrix polymer and thereby its swellability in the physiological environment of the plant. By selective use of polyester with known chemical structure and physical characteristics the skilled artisan can predetermine the degradation rate of the molded articles up to their complete solubilization and thus adapt them to the desired purpose.

The physical active substance/carrier/auxiliary agent-combinations representing the molded articles according to the present invention form a rather rigid, mechanically stable, but simultaneously formable compound. This composite structure can be processed into different three-dimensional structures.

Figure 2:
Figure 3:
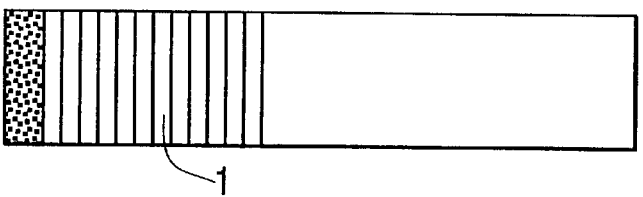

All embodiments may have a multilayer structure, with at least one layer of the laminate comprising a systemic active substance. The individual composite layers may be connected and coherent, or they may also be subdivided into segments (compartments; 1 in FIGS. 1 to 3). There are no limits with respect to varying the mutual arrangement of the individual compartments to one another. For example, they may have a so-called "core"-structure wherein one layer of the laminate is surrounded or enclosed by one lying above or below, thus forming a core (cf. FIG. 1). Another segmental arrangement is an alternating layer sequence (cf. FIGS. 2 and 3).

By combining several compartments active substances can easily be combined, and segments of different active substance concentration can be obtained. The individual compartments may vary extremely with respect to their active substance release rate. It is not absolutely necessary that all of the compartments comprise active substances.

When compartments having a different release profile are used, different active substances can be released with one implant at a predetermined time sequence; this is of particular advantage, e.g. in the therapy of different but in combination appearing plant diseases.

The implants according to the present invention may be obtained as molded pieces of different shape. Small rods, plates, spheres of different sizes, or granulates are preferred molded pieces. Most suitably, the sections are dimensioned such that they can easily be handled by hand. In general the particle size amounts to 0.1 to 50 mm, preferably 0.2 to 20 mm.

Figure 4:
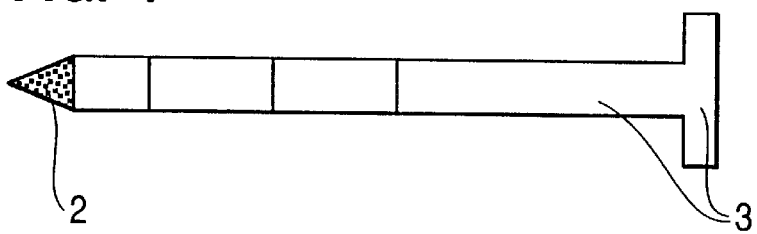

Among the suitable configurations forms of a nail or screw stand out in particular since these promote application and are very easy to handle. A particularly favorable molded article is the form of a nail (FIG. 4) whose tip 2 is rendered mechanically resistant. The mechanical resistance may be obtained by a coating of hard material, e.g., metal. This embodiment is of particular advantage because special implantation devices can be omitted and the application carried out by a nonexpert. Another advantage of this embodiment lies in the fact that the cavity resulting in the trunk of the plant during application is sealed by the nail head in a tight manner, thus excluding the potential risk of active substance exudation.

Figure 5:
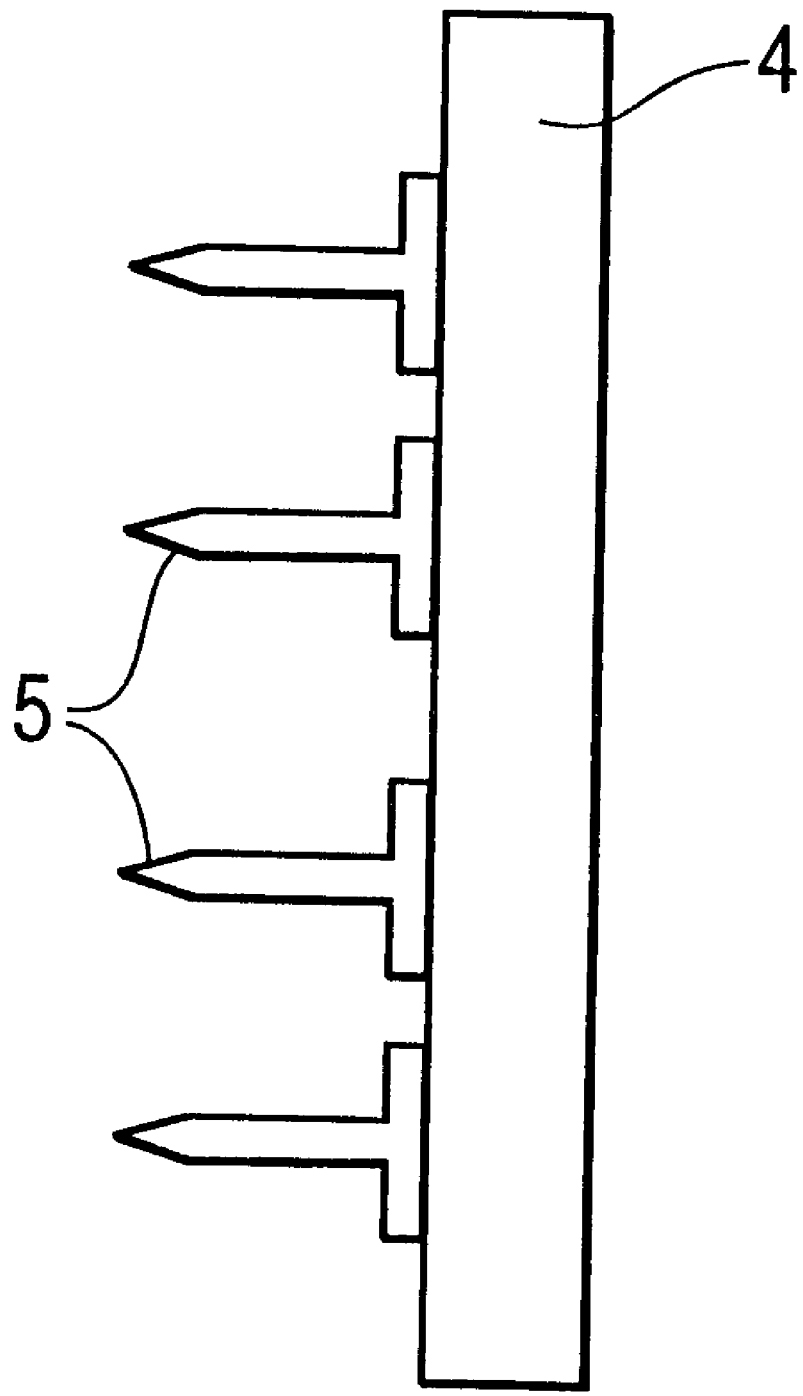

Another particularly advantageous embodiment of the implants according to the present invention is a device wherein several nail-shaped members 5 are connected with one another by fastening them on or in a rigid plate 4 (FIG. 5). The plate may have different dimensions depending on the number of implants to be applied. The plate is made of a mechanically resistant material which is compatible with plant tissues. Wood is to be mentioned as a particularly suitable material for this purpose. The particular advantage of this embodiment lies in the fact that the insertion of the bodies into the woody trunks of the plants is considerably facilitated. This embodiment is particularly advantageous because several nail-shaped members which—owing to their small size—are difficult to handle individually are integrated into one application unit. Moreover, the power of impact is distributed on the individual components in a relatively even manner, thus minimizing the risk of tissue damage caused by excessive mechanical action.

The molded articles according to the present invention exhibit thermoplastic processibility and can therefore be produced according to different methods, e.g., by extrusion, compression, and injection molding.

The molded articles according to the present invention may advantageously be used to administer bioactive substances to plants. The active substances may be plant protection agents in general (insecticides, fungicides, bactericides, acaricides), plant restoratives, and growth-influencing agents (phytohormones, fertilizers). These intracorporeal release systems are preferably used in case a conventional application technique is not possible or not reliable or not suitable. For this reason a particular field of application are municipal park grounds where plant protection measures in trees by means of conventional techniques are difficult to carry out. These biodegradable implants are excellently suitable for the long-term treatment of plants, in particular of trees, e.g. in fruit growing and forestry where certain seasonal diseases are occurring at regular intervals.

The molded articles according to the present invention are implanted into the plant's shoot axis, the preferred implantation site being the young shoot base. The implants are particularly suitable for the use in plants having lignified sprouts (shrubs and trees).

The present invention will be illustrated in greater detail by the following examples:

EXAMPLE 1

60 g of poly-(3-hydroxybutanoic acid) (PHB) and 40 g of polyvinyl acetate are dissolved in 20 g of chloroform. The solution is carefully concentrated by evaporation at a temperature of 30° C. and afterdried under vacuum. The compact compound thus obtained is pulverized in a ball mill; under addition of 6 g of polyethyleneglycol 400 (PEG 400) and 18 g of fosetyl-Al, it is then heated at a temperature of 180° C. in a suitable device, e.g. an extruder for thermoplastics, until a moldable mass is obtained. The active substance fosetyl-Al is homogeneously dispersed in the softened polymer by means of kneading. The active substance/polymer-suspension so obtained is then pressed through a die of suitable diameter (>2 mm). The resulting strand is reduced into rod-shaped aggregates whose active substance content is determined by their dimensions.

EXAMPLE 2

A commercially available chitin nonwoven fabric is pulverized in a ball mill, and 25 g of a copolymer of 75 mole-% of lactide and 25 mole-% of glycolide and 20 g of triticonazole are added to 375 g of this powder. The mixture thus obtained is sufficiently homogenized. In a heated press at 135° C. under a pressure of about 630 bar, it is then molded in a metal negative mold into nail-shaped fragments for two minutes; each of the molded articles comprises 89.2%-wt. of polymer, 6.0%-wt. of copolymer, and 4.5%-wt. of thiabendazol.

EXAMPLE 3

A mixture consisting of 64%-wt. of poly-$\epsilon$-caprolactone, 22%-wt. of polylactic acid, 4%-wt. of glycerol, and 10%-wt. of the active substance fosetyl-Al is molten in an extruder at a temperature of 120 to 145° C. and then drawn out in a spread coater to form a film of 2,000 $\mu$m thickness. After cooling the film is cut into rod-shaped portions. The fragments so obtained are optionally formed into rolls.

We claim:

1. An implantable thermoplastically molded article for the administration of an active substance to a plant wherein the molded article is at least partially biologically degradable within the plant comprising
    a) 0.5 to 90%-wt. of a polymer matrix comprising 30 to 80%-wt., based on the polymer content, of a hydrophobic polymer,
    b) 0.5 to 15%-wt. of at least one active substance dissolved or homogeneously dispersed in the polymer matrix, the release of said active substance is controlled by the biodegradation rate of said polymer matrix, and
    c) 0.0 to 50%-wt. of an auxiliary agent.
2. The molded article according to claim 1, wherein the hydrophobic polymer is 50 to 65%-wt of component a).
3. The molded article according to claim 1, wherein the polymer matrix comprises at least one polymer selected from the group consisiting of homopolymers and copolymers of polylactic acid, polyglycolic acid, polylactides, poly $\alpha$-hydroxyfatty acids having 2 to 16 carbon atoms, polyamides, polyorthoesters, polyanhydrides, starch, lignin, chitin, cellulose and derivatives of cellulose.
4. The molded article according to claim 1, wherein the hydrophobic polymer is selected from the group consisting of aliphatic polyesters, cellulose derivatives with a degree of substitution of $\leqq 2$, chitin, lignin from the Kraft process and polyanhyrides.
5. The molded article according to claim 4, wherein the aliphatic polyester is selected from the group consisting of polycaprolactone, polyhydroxybutanoic acid, polyhydroxybutanoic acid/hydroxyvaleric acid copolymer and polylactic acid.
6. The molded article according to claim 4, wherein the celluloses derivatives are selected from the group consisting of cellulose ether, cellulose ester, and cellulose acetate/butyrate-mixed ester.
7. The molded article according to claim 1, wherein the active substance is at least one substance selected from the group consisting of an insecticide, a fungicide, a bactericide, an acaricide and a growth regulator.
8. The molded article according to claim 7, wherein the insecticide is selected from the group consisting of butocaroxim, dimethoate, fenoxycarb, methamyl, oxamyl, oxydemeton-methyl, pirimicarb and propoxur.
9. The molded article according to claim 7, wherein the fungicide is selected from the group consisting of benomyl, bromuconazole, bitertanole, etaconazole, flusilazol, furalaxyl, fosetyl-Al, imazalil, metalaxyl, penconazole, propiconazole, thiabendazol, triadimefon, triadimenol and triforine.
10. The molded article according to claim 7, wherein the bactericide is flumequine.
11. The molded article according to claim 7, wherein the acaricide is selected from the group consisting of clofentizine, fenbutatin oxide and hexythiazox.
12. The molded article according to claim 7, wherein the growth regulator is selected from the group consisting of ethephon and $\beta$-indolylacetic acid (IAA).
13. The molded article according to claim 1, wherein the molded article has at least two compartments and at least one compartment comprises an active substance.
14. The molded article according to claim 13, wherein the molded article has more than one compartment each active substance containing compartments have different kinetic release rates.

15. The molded article according to claim 1, wherein the molded article has the shape of a rod, a plate, a sphere, a nail or a granulate.

16. The molded article according to claim 13, wherein the molded article has the shape of a nail wherein the tip (2) is mechanically resistant and the shank and head has compartments (3).

17. A device for adminstering an active substance to a plant by implanting into said plant a molded article which will release an active substance to said plant, said device comprising one or more molded nail-shaped molded articles according to claim 16 (5) which are connected to one another via a support (4).

18. A method of treating a plant with an active substance comprising implanting an molded article according to claim 1 into said plant.

19. A method of treating a plant with an active substance according to claim 18 wherein the molded article is implanted into the shoot base of the plant.

20. A method of treating a plant with an active substance comprising implanting an molded article according to claim 17 into said plant.

\* \* \* \* \*